United States Patent
Allen et al.

(10) Patent No.: US 11,048,874 B2
(45) Date of Patent: Jun. 29, 2021

(54) MEDICAL RECORD ERROR DETECTION SYSTEM AND METHOD

(71) Applicant: International Business Machines Corporation, Armonk, NY (US)

(72) Inventors: Joshua S. Allen, Durham, NC (US); Kimberly S. Holmes, Raleigh, NC (US); Andrew J. Lavery, Austin, TX (US); Fernando J. Suarez Saiz, Armonk, NY (US)

(73) Assignee: International Business Machines Corporation, Armonk, NY (US)

( * ) Notice: Subject to any disclaimer, the term of this patent is extended or adjusted under 35 U.S.C. 154(b) by 875 days.

(21) Appl. No.: 14/988,312

(22) Filed: Jan. 5, 2016

(65) Prior Publication Data
US 2017/0193174 A1    Jul. 6, 2017

(51) Int. Cl.
*G16H 10/60*    (2018.01)
*G06F 40/279*    (2020.01)
*G16H 50/20*    (2018.01)

(52) U.S. Cl.
CPC .......... *G06F 40/279* (2020.01); *G16H 10/60* (2018.01); *G16H 50/20* (2018.01)

(58) Field of Classification Search
CPC .............................................. G06Q 50/22–24
See application file for complete search history.

(56) References Cited

U.S. PATENT DOCUMENTS

| 8,046,242 B1 | 10/2011 | daCosta et al. |
| 8,768,782 B1 * | 7/2014 | Myslinski ............... G06Q 10/10 705/26.1 |

(Continued)

FOREIGN PATENT DOCUMENTS

| WO | 2014111933 A1 | 7/2014 |

OTHER PUBLICATIONS

Luciani, D. et al. Automated interviews on clinical case reports to elicit directed acyclic graphs. Artificial Intelligence in Medicine, vol. 55, No. 1, 2012, pp. 1-11 [online], [retrieved on Mar. 23, 2019], Retrieved from the Internet. (Year: 2012).*

(Continued)

*Primary Examiner* — Robert W Morgan
*Assistant Examiner* — Emily Huynh
(74) *Attorney, Agent, or Firm* — Troutman Pepper Hamilton Sanders LLP

(57) ABSTRACT

Embodiments provide a system and method for medical record error detection. Using a cognitive system having natural language processing capabilities, the error detection system can analyze a corpus of medical records, which can correspond to a particular patient, as well as a new medical record, and parse each into one or more record elements. By comparing the record elements, the error detection system can detect one or more potential errors resulting from a record element in the new medical record being inconsistent or contradictory with the record elements in the prior medical records, or ambiguous. The error detection system can output a list of candidate answers for correcting the one or more potential errors based upon a cognitive analysis of the corpus of medical records. The error detection system can further output a list of suggested therapies based on the selection of one or more of the candidate answers.

19 Claims, 5 Drawing Sheets

(56) References Cited

U.S. PATENT DOCUMENTS

| | | | | |
|---|---|---|---|---|
| 9,002,773 B2* | 4/2015 | Bagchi | ............ | G06F 16/31 706/52 |
| 2011/0060584 A1* | 3/2011 | Ferrucci | ............ | G06F 17/273 704/9 |
| 2013/0007055 A1* | 1/2013 | Brown | ............ | G06F 16/3344 707/769 |
| 2013/0198599 A1* | 8/2013 | Kumar | ............ | G06F 40/177 715/227 |
| 2013/0262364 A1* | 10/2013 | Verbeek | ............ | G06N 5/04 706/46 |
| 2014/0278448 A1* | 9/2014 | Sadeghi | ............ | G06Q 50/22 705/2 |
| 2015/0356252 A1* | 12/2015 | Beker | ............ | G06F 19/00 705/3 |
| 2016/0125169 A1* | 5/2016 | Finn | ............ | G06F 16/951 707/692 |
| 2017/0046484 A1* | 2/2017 | Buckler | ............ | G06F 19/321 |
| 2017/0116519 A1* | 4/2017 | Johnson | ............ | G06F 16/35 |
| 2017/0185868 A1* | 6/2017 | Wang | ............ | G06K 9/6262 |
| 2017/0372007 A1* | 12/2017 | Lu | ............ | G16H 20/40 |
| 2018/0322942 A1* | 11/2018 | Stankiewicz | ............ | G06F 40/177 715/227 |

OTHER PUBLICATIONS

Mabotuwana, T. et al. "Mapping Institution-Specific Study Descriptions to RadLex Playbook Entries," Journal of Digital Imaging, vol. 27, No. 3, pp. 321-330 (2014). (Year: 2014).*

Wong et al., "Statistical Semantic and Clinical Confidence Analysis for Real-Time Clinical Progress Note Cleaning," Center for Software Practice, University of Western Australia, pp. 1-17, 2010 (retrieved from the Internet: http://www.academia.edu/2838431/Statistical_Semantic_and_Clinical_Confidence_Analysis_for_Real-Time_Clinical_Progress_Note_Cleaning).

* cited by examiner

MEDICAL RECORD ERROR DETECTION SYSTEM AND METHOD

TECHNICAL FIELD

The present application relates generally to a system and method that can be used detect and correct errors in medical records.

BACKGROUND

Medical professionals typically annotate a patient's medical record with notes after every action, test, or visit. However, as in every other human endeavor, mistakes can occur. Because it might be a period of months or years before the medical professional sees a particular patient again, these mistakes can go unnoticed for a long period of time, which can lead to adverse medical events. A medical professional who does not see a particular patient frequently might forget about that patient's information in the interim time, and will use the notes taken at the previous session to refresh his or her memory. However, in doing so, the medical professional may not realize that the previously-made error in the medical records is in-fact an error, and may incorrectly treat the patient based on that error.

Likewise, a clinic receiving a third-party provider's records will have little-to-no context in which to evaluate the records' accuracies. The new clinic and its medical professionals may make decisions without any background to know whether the received clinic note contained incorrect information. Existing solutions have involved manual correction of the clinic note if an error is discovered. However, as medical records may be repeatedly copied, manual correction only corrects that particular copy of the records. As medical professionals copy and paste information between records, the error can propagate quickly.

SUMMARY

Embodiments can provide a method in a data processing system comprising a processor and a memory comprising instructions which are executed by the processor to cause the processor to implement a medical record error detection system, which can comprise the steps of utilizing, through a cognitive system, natural language processing to analyze a corpus of prior medical records to identify one or more record elements; analyzing a new medical record along with the corpus of prior medical records to identify the one or more record elements present in the new medical record; comparing the one or more record elements of the new medical record with the one or more medical record elements identified in the corpus of prior medical records; and outputting one or more error messages based upon one or more record elements in the new medical record containing a potential error.

Embodiments can further provide a method wherein the potential error can result from the record element of the new medical record being inconsistent with respect to the corresponding one or more record elements in the corpus of prior medical records.

Embodiments can further provide a method wherein the potential error can result from the record element of the new medical record being contradictory with respect to the corresponding one or more record elements in the corpus of prior medical records.

Embodiments can further provide a method wherein the potential error can result from the record element of the new medical record being ambiguous.

Embodiments can further provide a method wherein the corpus of prior medical records and the new medical record can correspond to a particular patient.

Embodiments can further provide a method wherein the corpus of prior medical records and the new medical record can be clinical notes entered by a medical professional.

Embodiments can further provide a method which can further comprise the steps of outputting, based upon an algorithmic analysis by the cognitive system using natural language processing, a list of ranked candidate answers corresponding to suggested corrections of the perceived error; and modifying the record element of the new medical record based on the selection of the candidate answer representing the proper correction of the perceived error.

Embodiments can further provide a method wherein the ranking of the candidate answers can be influenced by one or more previous selections of candidate answers to correct one or more previously detected errors.

Embodiments can further provide a method which can further comprise outputting one or more suggested treatment options based on the modification of the record element of the new medical record.

Embodiments can further provide a method which can further comprise outputting, along with the list of ranked candidate answers, one or more explanations corresponding to each member of the list of candidate answers having evidentiary information derived from one or more sources of medical information.

In another illustrative embodiment, a computer program product comprising a computer usable or readable medium having a computer readable program is provided. The computer readable program, when executed on a processor, causes the processor to perform various ones of, and combinations of, the operations outlined above with regard to the method illustrative embodiment.

In yet another illustrative embodiment, a system is provided. The system may comprise a medical record error detection processor configured to perform various ones of, and combinations of, the operations outlined above with regard to the method illustrative embodiment.

Additional features and advantages of this disclosure will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF EXEMPLARY EMBODIMENTS

Figure 1:
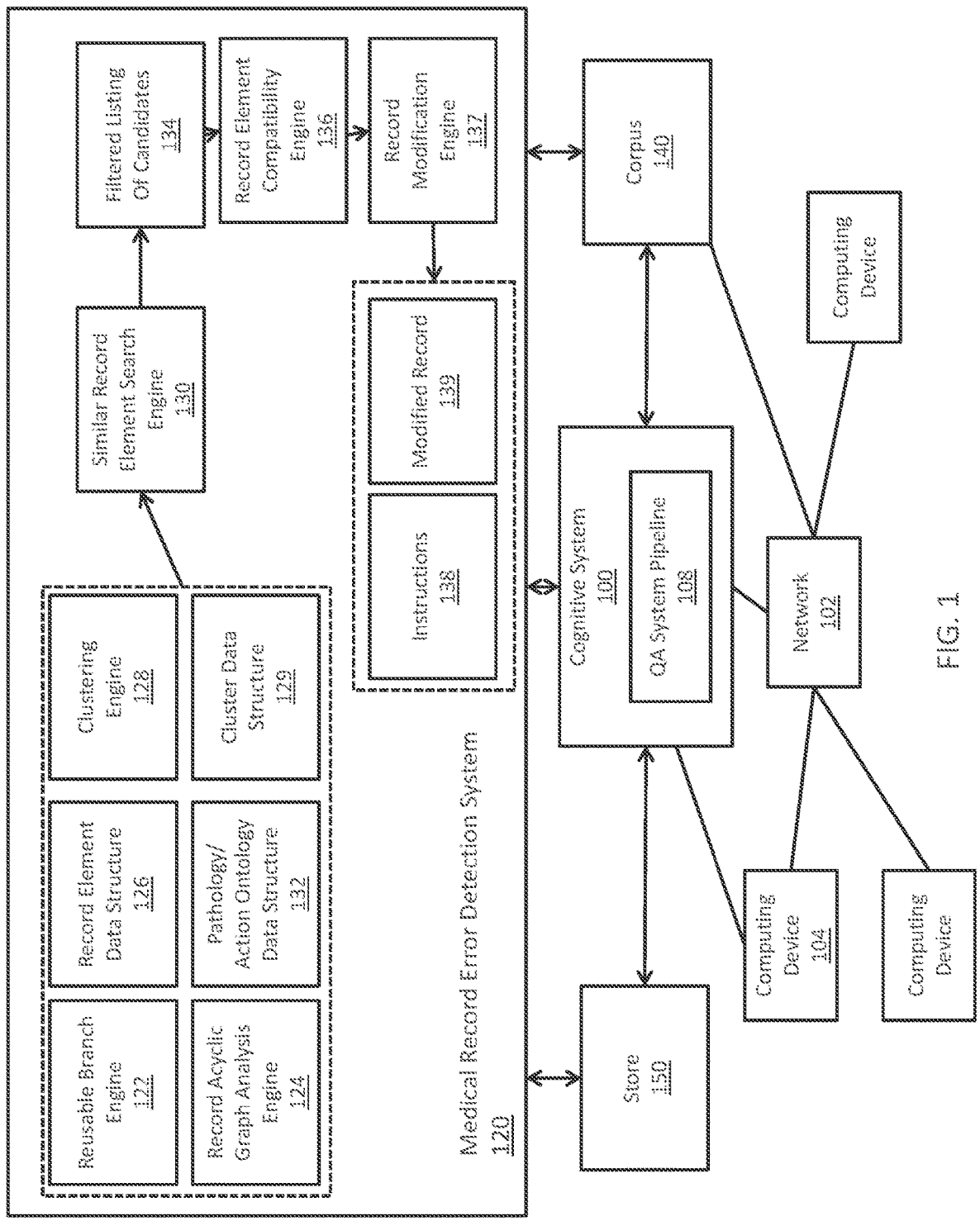
FIG. 1 depicts a schematic diagram of one illustrative embodiment of a cognitive system implementing a Question Answering (QA) pipeline in a computer network.

The present description and claims may make us of the terms "a," "at least one of," and "one or more of," with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within in the scope of the description and claims.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the example provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a head disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network (LAN), a wide area network (WAN) and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-along software package, partly on the user's computer and partly on a remote computer, or entirely on the remote computer or server. In the latter scenario, the remote computer may be connected to the user's computer through any type of network, including LAN or WAN, or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operations steps to be performed on the computer, other programmable apparatus, or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical functions. In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. IBM Watson™ is an example of one such cognitive system which can process human readable language and identify inferences between text passages with human-like accuracy at speeds far faster than human beings and on a much larger scale. In general, such cognitive systems are able to perform the following functions:

Navigate the complexities of human language and understanding
  Ingest and process vast amounts of structured and unstructured data
  Generate and evaluate hypotheses
  Weigh and evaluate responses that are based only on relevant evidence
  Provide situation-specific advice, insights, and guidance
  Improve knowledge and learn with each iteration and interaction through machine learning processes
  Enable decision making at the point of impact (contextual guidance)
  Scale in proportion to the task
  Extend and magnify human expertise and cognition
  Identify resonating, human-like attributes and traits from natural language
  Deduce various language specific or agnostic attributes from natural language
  High degree of relevant recollection from data points (images, text, voice) (memorization and recall)
  Predict and sense with situation awareness that mimic human cognition based on experiences
  Answer questions based on natural language and specific evidence In one aspect, cognitive systems provide mechanisms for answering questions posed to these cognitive systems using a Question Answering pipeline or system (QA system). The QA pipeline or system is an artificial intelligence application executing on data processing hardware that answers questions pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area (e.g., financial domain, medical domain, legal domain, etc.) where the body of knowledge (knowledgebase) can be organized in a variety of configurations, e.g., a structured repository of domain-specific information, such as ontologies, or unstructured data related to the domain, or a collection of natural language documents about the domain.

Content users input questions to the cognitive system which implements the QA pipeline. The QA pipeline then answers the input questions using the content in the corpus or data by evaluating documents, sections of documents, portions of data in the corpus, or the like. When a process evaluates a given section of a document for semantic content, the process can use a variety of conventions to query such document from the QA pipeline, e.g., sending the query to the QA pipeline as a well-formed question which is then interpreted by the QA pipeline and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using natural language processing.

As will be described in greater detail hereafter, the QA pipeline receives an input question, parses the question to extract the major features of the question, uses the extracted features to formulate queries, and then applies those queries to the corpus of data. Based on the application of the queries to the corpus of data, the QA pipeline generates a set of hypotheses, or candidate answers to the input question, by looking across the corpus of data for portions of the corpus of data that have some potential for containing a valuable response to the input question. The QA pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response, i.e. candidate answer, is inferred by the question. This process is repeated for each of the candidate answers until the QA pipeline identifies candidate answers that surface as being significantly stronger than others and thus generates a final answer, or ranked set of answers, for the input question.

As mentioned above, QA pipeline and mechanisms operate by accessing information from a corpus of data or information (also referred to as a corpus of content), analyzing it, and then generating answer results based on the analysis of this data. Accessing information from a corpus of data typically includes: a database query that answers questions about what is in a collection of structured records, and a search that delivers a collection of document links in response to a query against a collection of unstructured data (text, markup language, etc.). Conventional question answering systems are capable of generating answers based on the corpus of data and the input question, verifying answers to a collection of questions for the corpus of data, correcting errors in digital text using a corpus of data, and selecting answers to questions from a pool of potential answers, i.e. candidate answers.

Content creators, such as article authors, electronic document creators, web page authors, document database creators, and the like, determine use cases for products, solutions, and services described in such content before writing their content. Consequently, the content creators know what questions the content is intended to answer in a particular topic addressed by the content. Categorizing the questions, such as in terms of roles, type of information, tasks, or the like, associated with the question, in each document of a corpus of data allows the QA pipeline to more quickly and efficiently identity documents containing content related to a specific query. The content may also answer other questions that the content creator did not contemplate that may be useful to content users. The questions and answers may be verified by the content creator to be contained in the content for a given document. These capabilities contribute to improved accuracy, system performance, machine learning, and confidence of the QA pipeline. Content creators, automated tools, or the like, annotate or otherwise generate metadata for providing information useable by the QA pipeline to identify these question and answer attributes of the content.

Operating on such content, the QA pipeline generates answers for input questions using a plurality of intensive analysis mechanisms which evaluate the content to identify the most probable answers, i.e. candidate answers, for the input question. The most probable answers are output as a ranked listing of candidate answers ranked according to their relative scores or confidence measures calculated during evaluation of the candidate answers, as a single final answer having a highest ranking score or confidence measure, or which is a best match to the input question, or a combination of ranked listing and final answer.

FIG. 1 depicts a schematic diagram of one illustrative embodiment of a cognitive system 100 implementing a question answering (QA) pipeline 108 in a computer network 102. One example of a question/answer generation operation which may be used in conjunction with the principles described herein is described in U.S. Patent Application Publication No. 2011/0125734, which is herein incorporated by reference in its entirety. The cognitive system 100 is implemented on one or more computing devices 104 (comprising one or more processors and one or more memories, and potentially any other computing device elements generally known in the art including buses, storage devices, communication interfaces, and the like) connected to the computer network 102. The network 102 includes multiple computing devices 104 in communication with each other and with other devices or components via one or more wired and/or wireless data communication links, where each communication link comprises one or more of wires, routers, switches, transmitters, receivers, or the like. The cognitive system 100 and network 102 enables question/answer (QA) generation functionality for one or more cognitive system users via their respective computing devices. Other embodiments of the cognitive system 100 may be used with components, systems, sub-systems, and/or devices other than those that are depicted herein.

The cognitive system 100 is configured to implement a QA pipeline 108 that receive inputs from various sources. For example, the cognitive system 100 receives input from the network 102, a corpus of electronic documents 140, cognitive system users, and/or other data and other possible sources of input. In one embodiment, some or all of the inputs to the cognitive system 100 are routed through the network 102. The various computing devices 104 on the network 102 include access points for content creators and QA system users. Some of the computing devices 104 include devices for a database storing the corpus of data 140. Portions of the corpus of data 140 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus of data 140 for use as part of a corpus of data with the cognitive system 100. The document includes any file, text, article, or source of data for use in the cognitive system 100. QA system users access the cognitive system 100 via a network connection or an Internet connection to the network 102, and input questions to the cognitive system 100 that are answered by the content in the corpus of data 140. In one embodiment, the questions are formed using natural language. The cognitive system 100 parses and interprets the question via a QA pipeline 108, and provides a response to the cognitive system user containing one or more answers to the question. In some embodiments, the cognitive system 100 provides a response to users in a ranked list of candidate answers while in other illustrative embodiments, the cognitive system 100 provides a single final answer or a combination of a final answer and ranked listing of other candidate answers.

The cognitive system 100 implements the QA pipeline 108 which comprises a plurality of stages for processing an input question and the corpus of data 140. The QA pipeline 108 generates answers for the input question based on the processing of the input question and the corpus of data 140. The QA pipeline 108 will be described in greater detail hereafter with regard to FIG. 3.

In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a QA pipeline of the IBM Watson™ cognitive system receives an input question, which it then parses to extract the major features of the question, and which in turn are then used to formulate queries that are applied to the corpus of data. Based on the application of the queries to the corpus of data, a set of hypotheses, or candidate answers to the input question, are generated by looking across the corpus of data for portions of the corpus of data that have some potential for containing a valuable response to the input question. The QA pipeline of the IBM Watson™ cognitive system then performs deep analysis on the language of the input question and the language used in each of the portions of the corpus of data found during the application of the queries using a variety of reasoning algorithms. The scores obtained from the various reasoning algorithms are then weighted against a statistical model that summarizes a level of confidence that the QA pipeline of the IBM Watson™ cognitive system has regarding the evidence that the potential response, i.e. candidate answer, is inferred by the question. This process is repeated for each of the candidate answers to generate ranked listing of candidate answers which may then be presented to the user that submitted the input question, or from which a final answer is selected and presented to the user. More information about the QA pipeline of the IBM Watson™ cognitive system may be obtained, for example, from the IBM Corporation website, IBM Redbooks, and the like. For example, information about the QA pipeline of the IBM Watson™ cognitive system can be found in Yuan et al., "Watson and Healthcare." IBM developerWorks, 2011 and "The Era of Cognitive Systems: An Inside Look at IBM Watson and How it Works" by Rob High, IBM Redbooks, 2012.

As shown in FIG. 1, in accordance with some illustrative embodiments, the cognitive system 100 is further augmented, in accordance with the mechanisms of the illustrative embodiments, to include logic implemented in specialized hardware, software executed on hardware, or any combination of specialized hardware and software executed on hardware, for implementing a medical record error detection system 120. The operation of the medical record error detection system 120 may be initiated in response to receiving a request or input question directed to one or more medical records for one or more medical patients. The request or input question may be provided via a graphical user interface through which a user selects a medical record for analysis, such as previously described above. Alternatively, the medical record error detection system 120 can perform automatic checks of all new or modified medical records as a matter of routine.

In response to the request or input question, the medical record error detection system 120 determines whether or not entries or portions of an entry in the particular medial record are contradictory or ambiguous, suggests alternate actions or therapy based on any modification, or determines the accuracy of the particular entry in relation to the entire medical record. Moreover, the medical record error detection system 120 further cognitively analyzes these aspects of the medical record with regard to possible modifications of the medical record to conform to the patient's known medical history and/or possible avenues of unconsidered action options. The medical record error detection system 120 can be further configured to statistically analyze evidence related to a patient's particular medical pathology in order to determine inconsistencies.

In one illustrative embodiment of the present invention, records in a corpus 140 of existing medical records are subjected to natural language processing techniques of the cognitive system 100 and/or medical record error detection system 120 to transform the medical records into acyclic graphs where nodes represent medical pathologies and actions (record elements), and connectors represent the sequence of actions, as previously mentioned above. This operation may be performed, for example, as part of an ingestion operation of the cognitive system 100 which reads the natural language text of the electronic documents in the corpus 140, parses the natural language text and performs natural language processing on the natural language text, including performing annotation operations using annotators, to extract key features of the natural language text which are then converted to the acyclic graphs of the various records in the corpus 140. For example, key features may include pharmaceuticals prescribed, medical actions performed, appointment times, diagnostic tests ordered, and terms/phrases representing linkages between the features, and combinations of the features.

The acyclic graphs of the medical records ingested from the corpus 140 are stored in storage device 150 associated with either the cognitive system 100 or the medical record error detection system 120, where the storage device 150 may be a memory, a hard disk based storage device, flash memory, solid state storage device, or the like (hereafter assumed to be a "memory" with in-memory representations of the acyclic graphs for purposes of description). The in-memory acyclic graphs are then analyzed by the reusable branch engine 122 of the medical record error detection system 120 to identify reusable branches within the acyclic graphs and a reusable branch data structure having entries for each reusable branch found in this way, and other reusable branches either found in other corpora, readily known and pre-populated in the reusable branch data structure by subject matter experts, or the like, is generated. The identification of the reusable branches may further be associated with the in-memory acyclic graph of the corresponding record as well so as to identify for the particular medical record what the reusable branches are in the medical record.

Either as part of the ingestion operation, or by the medical record acyclic graph analysis engine 124 analyzing the acyclic graphs generated by the ingestion operation, a record element data structure 126 defining the various pathologies and actions in the ingested medical record corpus 140, as well as other record elements pre-populated in the record element data structure 126 either through analysis of other corpora or through manual input by subject matter experts, is generated. The pathologies and actions in the record element data structure 126 have characteristics determined by the record acyclic graph analysis engine 124 in accordance with knowledge bases of pathologies/actions. These characteristics may include information regarding the type of the pathology/action (record elements), e.g., an imaging modality, a pharmaceutical regimen, etc. The characteristics may be provided at any desired granularity such that there may be multiple types within an overall general category of types, e.g., for the category of imaging, there may be a type of "invasive" or "non-invasive". In some cases, rather or in addition to having the knowledge bases of pathologies/actions, the types of pathologies/actions may be determined by the record acyclic graph analysis engine 124, or as part of the ingestion operation, when parsing and analyzing the text of a record which may include subsection headers or other text that references a specific category or type of the pathology/action.

The record element data structure 126 is analyzed by clustering engine 128 to identify clusters of record elements based on their characteristics. For example, record elements may be clustered according to similar record element types to form record element clusters. These clusters may be stored in a cluster data structure 129. For example, cardiological pathologies may form one cluster, oncological pathologies may form another cluster, and the like. As noted above, some record elements may have sub-elements and various levels of clustering may be performed, which may be classified/clustered into other clusters. Thus, the same record element may be present in multiple clusters.

When a user or the system wishes to modify an existing medical record with the addition of a new record element or replace an existing record element with a new record element, in response to receiving the request or input question to the cognitive system 100, the request is parsed and analyzed using natural language processing techniques to identify the nature of the request/question, i.e. the nature of the request/question is a modification to an existing medical record. The request/question specifies the medical record to be modified and one or more record elements to be added/replaced in the existing medical record.

In response to receiving the input request/question and determining the medical record to be modified and the medical record element(s) that are the subject of the modification, a similar medical record element search engine 130 performs a search of the cluster data structure 129 to generate a listing of the medical record element clusters that involve the given new medical record element(s). In making this list, the similar medical record element search engine 130 may analyze the clusters of reusable branches that contain the new medical record element to produce an initial list of candidate medical record elements. This listing is then extended with candidate medical record elements for similar medical record elements obtained from clusters with which the elements of the reusable branches involving the new medical record element are clustered.

Alternatively, the clustering performed by the clustering engine 128 may be performed after the identification of similar medical record elements to those of the reusable branches found as having the new medical record element(s), performed by the similar medical record element search engine 130 and the list may then be extended with candidate medical record elements for similar medical record elements by using a provided pathology/action ontology data structure 132. Those candidate elements may be included in the listing and the listing may be analyzed by the clustering engine 128 to generate clusters of medical record elements for storage in the duster data structure 129.

In either case, the similar medical record element search engine 130 then determines whether the original existing medical record that is to be modified already contains any of the clusters of candidate medical record elements, i.e. the clusters identified as having the new medical record element(s) in the request. For those that are already present within the existing medical record, the candidate clusters may be eliminated from the listing to generate a filtered listing of candidate medical record elements and their clusters 134.

The medical record element clusters remaining in the filtered listing of candidate medical record elements 134 are then analyzed by a medical record element compatibility engine 136 to identify which of the element clusters are compatible with the department type of the original existing medical record that is to be modified. The medical record element compatibility engine 136 may utilize configured association rules learned during a training of the medical record error detection system 120 and knowledge base, where the association rules specify compatibility of medical record elements with different department types. Using these association rules, the medical record element compatibility engine determines what combinations or patterns of one or more medical record elements are found in medical records of the same department type as the original existing medical record, e.g., if the original existing medical record is a oncology medical record, then combinations or patterns of medical record elements are identified in other oncology medical records. The intersection of the association rules with the candidate medical record element clusters indicates which element clusters are compatible with the department type of the original existing medical record that is being modified. The resulting candidate clusters that intersect with the association rules may then be ranked by the medical record element compatibility engine 136, such as based on frequency of appearance of the clusters, or medical record elements in the cluster, in the medical record corpus 140 as a whole, or in medical records of the medical record corpus 140 that have a similar department type as the department type of the original existing medical record. Other ranking criteria may also be utilized as noted above.

A medical record element cluster in the filtered listing of candidate clusters 134, which also intersects with one or more of the association rules, is selected by the medical record element compatibility engine 136 for use in modifying the original existing medical record. This selection may be based on the ranking of the clusters intersecting the association rules as discussed above. For example, a top ranked cluster may be selected for further use in modifying the original existing medical record. Alternatively, other selection criteria may be utilized as well, such as in an implementation where ranking of the clusters may not be performed, as previously discussed above.

From the selected cluster, a representative element and/or reusable branch is selected by the medical record modification engine 137 from the cluster to represent the element that will be added to the existing medical record that is to be modified, either by adding in the additional element or replacing an existing element of the medical record with the new selected element from the selected cluster. The reusable branch corresponding to the selected representative element of the cluster is then used by the medical record modification engine 137 to generate instructions needed to prepare the selected medical record element represented by the selected cluster. The instructions 138 corresponding to the selected representative element and its reusable branch are merged by the medical record modification engine 137 into the original existing medical record as a new medical record section or branch and a corresponding modified acyclic graph and natural language text corresponding to the modified medical record is generated 139. Similarly, the listing of elements for the medical record is updated to include the additional elements present in the new sub-tree or branch as well to generate a modified listing of elements associated with the modified medical record.

The modified medical record may then be returned to the original requestor or source of the input request/question as a response/answer to the input request/question. The modified medical record may include the natural language text for the modified medical record provided in a natural language text format, for example. In general, the acyclic graph of the modified medical record is not returned to the requestor or source of the input request/question since it is an internal representation of the medical record for purposes of processing. However, if desired, the acyclic graph data structure for the modified medical record may also be provided back to the requestor/source. The modified medical record may be returned as part of a graphical user interface or other suitable output that provides natural language text and/or graphical representations for representing the modified medical record.

Thus, the mechanisms of the illustrative embodiments provide an intelligent cognitive system for detecting errors in medical records, modifying existing medical records to include new or replacement medical record elements (pathologies/actions) into the existing medical records to generate modified new medical records taking into consideration the drafting style of the medical professional and clinic, the department of medicine the records originated from, and the context of the other medical record elements and the medical record as a whole.

Figure 2:
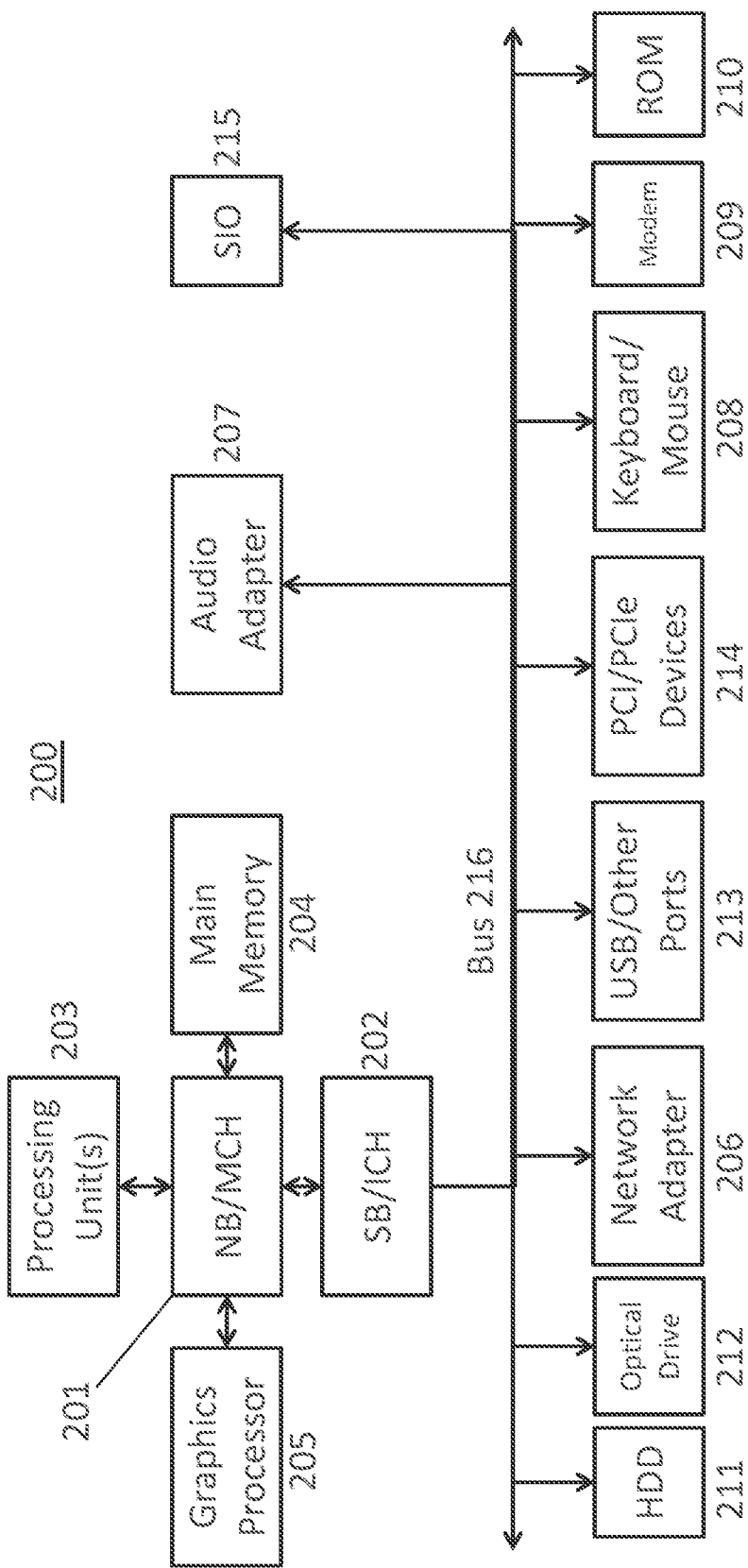
FIG. 2 is a block diagram of an example data processing system in which aspects of the illustrative embodiments are implemented.

FIG. 2 is a block diagram of an example data processing system 200 in which aspects of the illustrative embodiments are implemented. Data processing system 200 is an example of a computer, such as a server or client, in which computer usable code or instructions implementing the process for illustrative embodiments of the present invention are located. In one embodiment, FIG. 2 represents a server computing device, such as a server, which implements the medical record error detection system 120 and cognitive system 100 described herein.

In the depicted example, data processing system 200 can employ a hub architecture including a north bridge and memory controller hub (NB/MCH) 201 and south bridge and input/output (I/O) controller hub (SB/ICH) 202. Processing unit 203, main memory 204, and graphics processor 205 can be connected to the NB/MCH 201. Graphics processor 205 can be connected to the NB/MCH through an accelerated graphics port (AGP).

In the depicted example, the network adapter 206 connects to the SB/ICH 202. The audio adapter 207, keyboard and mouse adapter 208, modem 209, read only memory (ROM) 210, hard disk drive (HDD) 211, optical drive (CD or DVD) 212, universal serial bus (USB) ports and other communication ports 213, and the PCI/PCIe devices 214 can connect to the SB/ICH 202 through bus system 216. PCI/PCIe devices 214 may include Ethernet adapters, add-in cards, and PC cards for notebook computers. ROM 210 may be, for example, a flash basic input/output system (BIOS). The HDD 211 and optical drive 212 can use an integrated drive electronics (IDE) or serial advanced technology attachment (SATA) interface. The super I/O (SIO) device 215 can be connected to the SB/ICH.

An operating system can run on processing unit 203. The operating system can coordinate and provide control of various components within the data processing system 200. As a client, the operating system can be a commercially available operating system. An object-oriented programming system, such as the Java™ programming system, may run in conjunction with the operating system and provide calls to the operating system from the object-oriented programs or applications executing on the data processing system 200. As a server, the data processing system 200 can be an IBM® eServer™ System p® running the Advanced Interactive Executive operating system or the Linux operating system. The data processing system 200 can be a symmetric multiprocessor (SMP) system that can include a plurality of processors in the processing unit 203. Alternatively, a single processor system may be employed.

Instructions for the operating system, the object-oriented programming system, and applications or programs are located on storage devices, such as the HDD 211, and are loaded into the main memory 204 for execution by the processing unit 203. The processes for embodiments of the medical record error detection system can be performed by the processing unit 203 using computer usable program code, which can be located in a memory such as, for example, main memory 204, ROM 210, or in one or more peripheral devices.

A bus system 216 can be comprised of one or more busses. The bus system 216 can be implemented using any type of communication fabric or architecture that can provide for a transfer of data between different components or devices attached to the fabric or architecture. A communication unit such as the modem 209 or network adapter 206 can include one or more devices that can be used to transmit and receive data.

Those of ordinary skill in the art will appreciate that the hardware depicted in FIG. 2 may vary depending on the implementation. Other internal hardware or peripheral devices, such as flash memory, equivalent non-volatile memory, or optical disk drives may be used in addition to or in place of the hardware depicted. Moreover, the data processing system 200 can take the form of any of a number of different data processing systems, including but not limited to, client computing devices, server computing devices, tablet computers, laptop computers, telephone or other communication devices, personal digital assistants, and the like. Essentially, data processing system 200 can be any known or later developed data processing system without architectural limitation.

Figure 3:
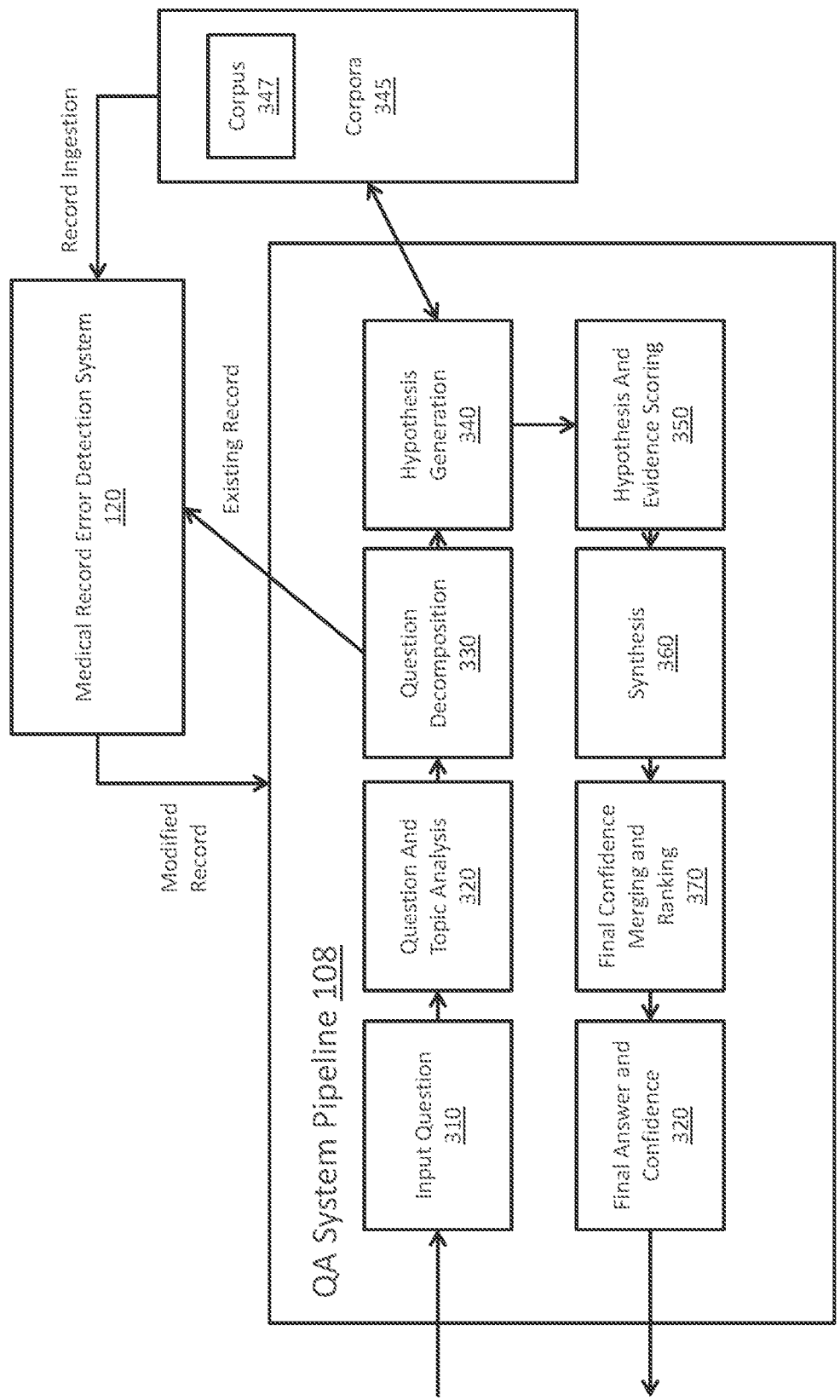
FIG. 3 illustrates a QA system pipeline, of a cognitive system, for processing an input question in accordance with one illustrative embodiment.

FIG. 3 illustrates a QA system pipeline, of a cognitive system, for processing an input question in accordance with one illustrative embodiment. The QA system pipeline of FIG. 3 may be implemented, for example, as QA pipeline 108 of cognitive system 100 in FIG. 1. It should be appreciated that the stages of the QA pipeline shown in FIG. 3 are implemented as one or more software engines, components, or the like, which are configured with logic for implementing the functionality attributed to the particular stage. Each stage is implemented using one or more of such software engines, components or the like. The software engines, components, etc., are executed on one or more processors of one or more data processing systems or devices and utilize or operate on data stored in one or more data storage devices, memories, or the like, on one or more of the data processing systems. The QA pipeline of FIG. 3 is augmented, for example, in one or more of the stages to implement the improved mechanism of the illustrative embodiments described hereafter, additional stages may be provided to implement the improved mechanism, or separate logic from the pipeline 108 may be provided for interfacing with the pipeline 108 and implementing the improved functionality and operations of the illustrative embodiments.

As shown in FIG. 3, the QA pipeline 108 comprises a plurality of stages 310-380 through which the cognitive system operates to analyze an input question and generate a final response. In an initial question input stage 310, the QA pipeline 108 receives an input question that is presented in a natural language format. That is, a user inputs, via a user interface, an input question for which the user wishes to obtain an answer, e.g., "Who are Washington's closest advisors?" In response to receiving the input question, the next stage of the QA pipeline 108, i.e. the question and topic analysis stage 320, parses the input question using natural language processing (NLP) techniques to extract major features from the input question, and classify the major features according to types, e.g., names, dates, or any of a plethora of other defined topics. For example, in the example question above, the term "who" may be associated with a topic for "persons" indicating that the identity of a person is being sought, "Washington" may be identified as a proper name of a person with which the question is associated, "closest" may be identified as a word indicative of proximity or relationship, and "advisors" may be indicative of a noun or other language topic.

In addition, the extracted major features include key words and phrases classified into question characteristics, such as the focus of the question, the lexical answer type (LAT) of the question, and the like. As referenced to herein, a lexical answer type (LAT) is a word in, or a word inferred from, the input question that indicates the type of the answer, independent of assigning semantics to that word. For example, in the question "What maneuver was invented in the 1500s to speed up the game and involves two pieces of the same color?" the LAT is the string "maneuver." The focus of a question is the part of the question that, if replaced by the answer, makes the question a standalone statement. For example, in the question "What drug has been shown to relieve the symptoms of ADD with relatively few side effects?," the focus is "drug" since if this word were replaced with the answer, e.g., the answer "Adderall" can be used to replace the term "drug" to generate the sentence "Adderall has been shown to relieve the symptoms of ADD with relatively few side effects." The focus often, but not always, contains the LAT. On the other hand, in many cases it is not possible to infer a meaningful LAT from the focus.

Referring again to FIG. 3, the identified major features are then used during the question decomposition stage 330 to decompose the question into one or more queries that are applied to the corpora of data/information 345 in order to generate one or more hypotheses. The queries are generated in any known or later developed query language, such as the Structure Query Language (SQL), or the like. The queries are applied to one or more databases storing information about the electronic texts, documents, articles, websites, and the like, that make up the corpora of data/information 345. That is, these various sources themselves, different collections of sources, and the like, represent a different corpus 347 within the corpora 345. There may be different corpora 347 defined for different collections of documents based on various criteria depending upon the particular implementation. For example, different corpora may be established for different topics, subject matter categories, sources of information, or the like. As one example, a first corpus may be associated with healthcare documents while a second corpus may be associated with financial documents. Alternatively, one corpus may be documents published by the U.S. Department of Energy while another corpus may be IBM Redbooks documents. Any collection of content having some similar attribute may be considered to be a corpus 347 within the corpora 345.

The queries are applied to one or more databases storing information about the electronic texts, documents, articles, websites, and the like, that make up the corpus of data/ information, e.g., the corpus of data 140 in FIG. 1. The queries are applied to the corpus of data/information at the hypothesis generation stage 340 to generate results identifying potential hypotheses for answering the input question, which can then be evaluated. That is, the application of the queries results in the extraction of portions of the corpus of data/information matching the criteria of the particular query. These portions of the corpus are then analyzed and used, during the hypothesis generation stage 340, to generate hypotheses for answering the input question. These hypotheses are also referred to herein as "candidate answers" for the input question. For any input question, at this stage 340, there may be hundreds of hypotheses or candidate answers generated that may need to be evaluated.

The QA pipeline 108, in stage 350, then performs a deep analysis and comparison of the language of the input question and the language of each hypothesis or "candidate answer," as well as performs evidence scoring to evaluate the likelihood that the particular hypothesis is a correct answer for the input question. As mentioned above, this involves using a plurality of reasoning algorithms, each performing a separate type of analysis of the language of the input question and/or content of the corpus that provides evidence in support of, or not in support of, the hypothesis. Each reasoning algorithm generates a score based on the analysis it performs which indicates a measure of relevance of the individual portions of the corpus of data/information extracted by application of the queries as well as a measure of the correctness of the corresponding hypothesis, i.e. a measure of confidence in the hypothesis. There are various ways of generating such scores depending upon the particular analysis being performed. In general, however, these algorithms look for particular terms, phrases, or patterns of text that are indicative of terms, phrases, or patterns of interest and determine a degree of matching with higher degrees of matching being given relatively higher scores than lower degrees of matching.

In the synthesis stage 360, the large number of scores generated by the various reasoning algorithms are synthesized into confidence scores or confidence measures for the various hypotheses. This process involves applying weights to the various scores, where the weights have been determined through training of the statistical model employed by the QA pipeline 108 and/or dynamically updated. For example, the weights for scores generated by algorithms that identify exactly matching terms and synonyms may be set relatively higher than other algorithms that are evaluating publication dates for evidence passages. The weights themselves may be specified by subject matter experts or learned through machine learning processes that evaluate the significance of characteristics evidence passages and their relative importance to overall candidate answer generation.

The weighted scores are processed in accordance with a statistical model generated through training of the QA pipeline 108 that identifies a manner by which these scores may be combined to generate a confidence score or measure for the individual hypotheses or candidate answers. This confidence score or measure summarizes the level of confidence that the QA pipeline 108 has about the evidence that the candidate answer is inferred by the input question, i.e. that the candidate answer is the correct answer for the input question.

The resulting confidence scores or measures are processed by a final confidence merging and ranking stage 370 which compares the confidence scores and measures to each other, compares them against predetermined thresholds, or performs any other analysis on the confidence scores to determine which hypotheses/candidate answers are the most likely to be the correct answer to the input question. The hypotheses/candidate answers are ranked according to these comparisons to generate a ranked listing of hypotheses/ candidate answers (hereafter simply referred to as "candidate answers"). From the ranked listing of candidate answers, at stage 380, a final answer and confidence score, or final set of candidate answers and confidence scores, are generated and output to the submitter of the original input question via a graphical user interface or other mechanism for outputting information.

Figure 4:
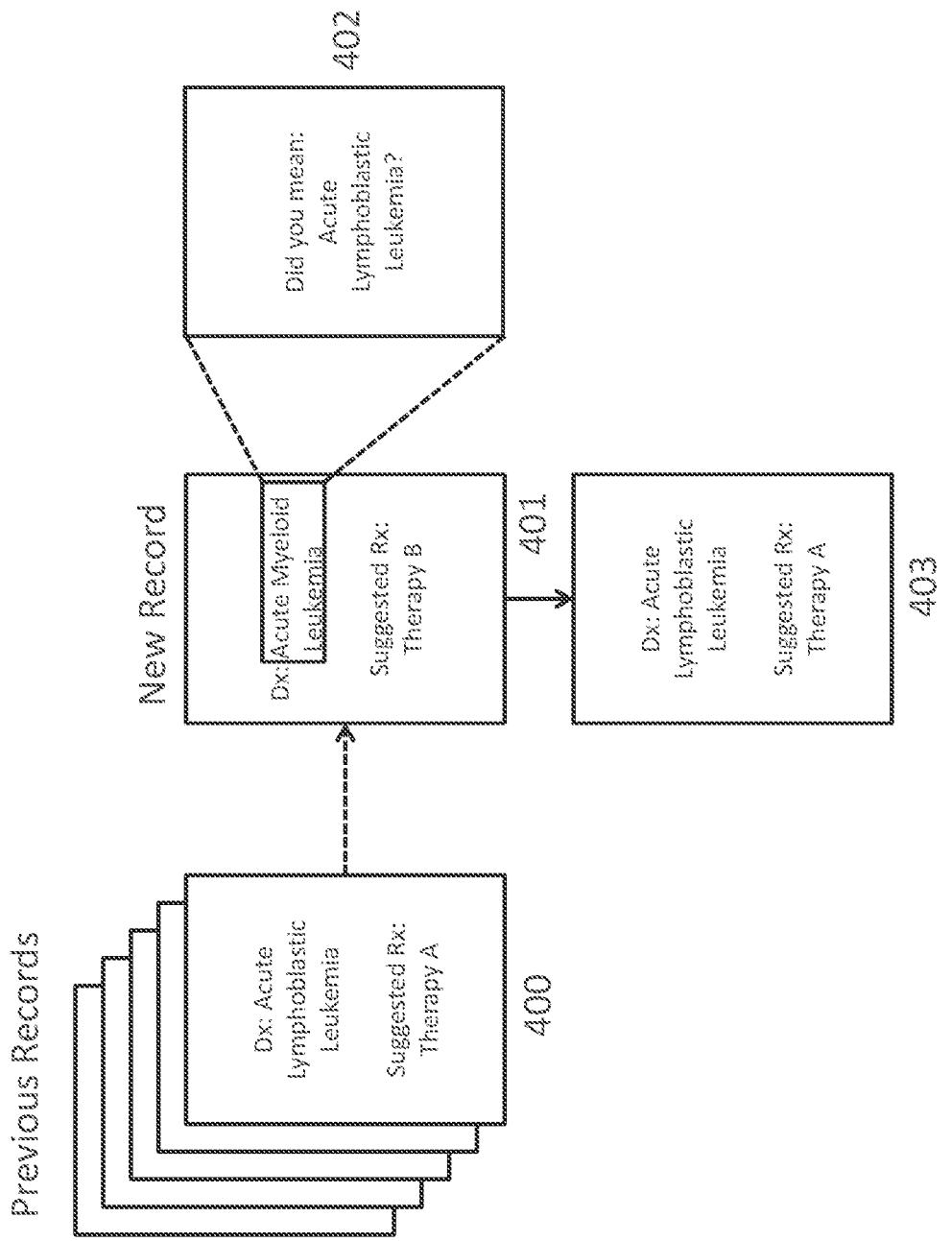
FIG. 4 illustrates an example diagram of an example suggested correction detected by the medical record error detection system based on a contradictory record entry.

FIG. 4 illustrates an example diagram of an example suggested correction detected by the medical record error detection system based on a contradictory record entry. As an example, the cognitive system 100 can be paired with a database containing medical records in the field of oncology, such as in the MD Anderson Oncology Expert Advisor (OEA). An OEA-like system can process patient information, including clinic notes/medical records, and can derive conclusions based upon that information, such as a suggested treatment. An OEA-like system can determine the patient's diagnosis, the past medical history of the patient, and use the cognitive system 100 to suggest treatments or therapies for the patient based upon the corpus of patient information.

Because differing diagnoses require differing treatments and therapies, the medical record error detection system can be used to correct erroneous medical records to prevent changes that would be detrimental to a patient's health. For example, while a patient's prior medical records 400 may have recorded a diagnosis of "acute lymphoblastic leukemia," a subsequent medical professional may subsequently enter or dictate a diagnosis of "acute myeloid leukemia" into a new medical record 401. As each form of leukemia has specific and mutually exclusive treatments, the propagation of this error could have dire consequences for the patient. Thus, the medical record error detection system, when comparing the new medical record 401 to the corpus of prior medical records 400 using natural language processing, can discern that there has been a diagnosis change in the pathology record element, and can provide a prompt 402 to the user of the medical record error correction system informing the user of the possible error. Identifying the error can allow the user to alter the new medical record 401 by providing the correct diagnosis and suggested therapy, and enter the correctly modified medical record 403 into the patient's file. Based on the entered diagnosis, whether modified to conform to previous diagnoses or left as entered due to the diagnosis having changed, the medical record error detection system can suggest alternate therapies to the user based upon the system analyzing the corpus of medical information.

As part of the error correction process, the medical record error detection system can be "trained" or have rules input into its corpus of data as to what medical information is likely to be contradictory and therefore incorrect. For example, if a leukemia patient is diagnosed as having acute myelogenous leukemia (AML), the patient should not be diagnosed as having a less severe myelodysplastic syndrome (MDS). Thus, the medical error detection system can be trained to always output an error message in a case where the prior medical records 400 of a patient denote the patient as having AML, but a new medical record is written with the patient being diagnosed with an MDS.

Additionally, the medical record error detection system can provide the user with relevant evidence as to why the medical record error is being flagged and corrected. For example, mutations in lung cancer patients are usually mutually exclusive. For instance, an epidermal growth factor receptor (EGFR) mutation is impossible if an anaplastic lymphoma kinase (ALK) translocation has occurred. The medical record error detection system, when presented with a medical record containing an error that it recognizes as impossible or contradictory, will prompt the user to correct the error. Additionally, the error detection system can display information from the corpus to evidence the necessity of the medical change, such as providing the user information as to why an EGFR mutation is impossible after an ALK translocation.

Likewise, the medical record error detection system can provide a notification when a particular medical record entry is inconsistent from previous record entries based on prior evidence. For example, if the medical records for a patient consistently list the patient as being prescribed "Medication A," a single medical record listing "Medication B", whether newly entered by a medical professional or found by the system in the body of prior medical records, can be identified and flagged as erroneous based upon the perceived inconsistency. The user can be prompted to correct that error such that the error does not propagate in the future.

Figure 5:
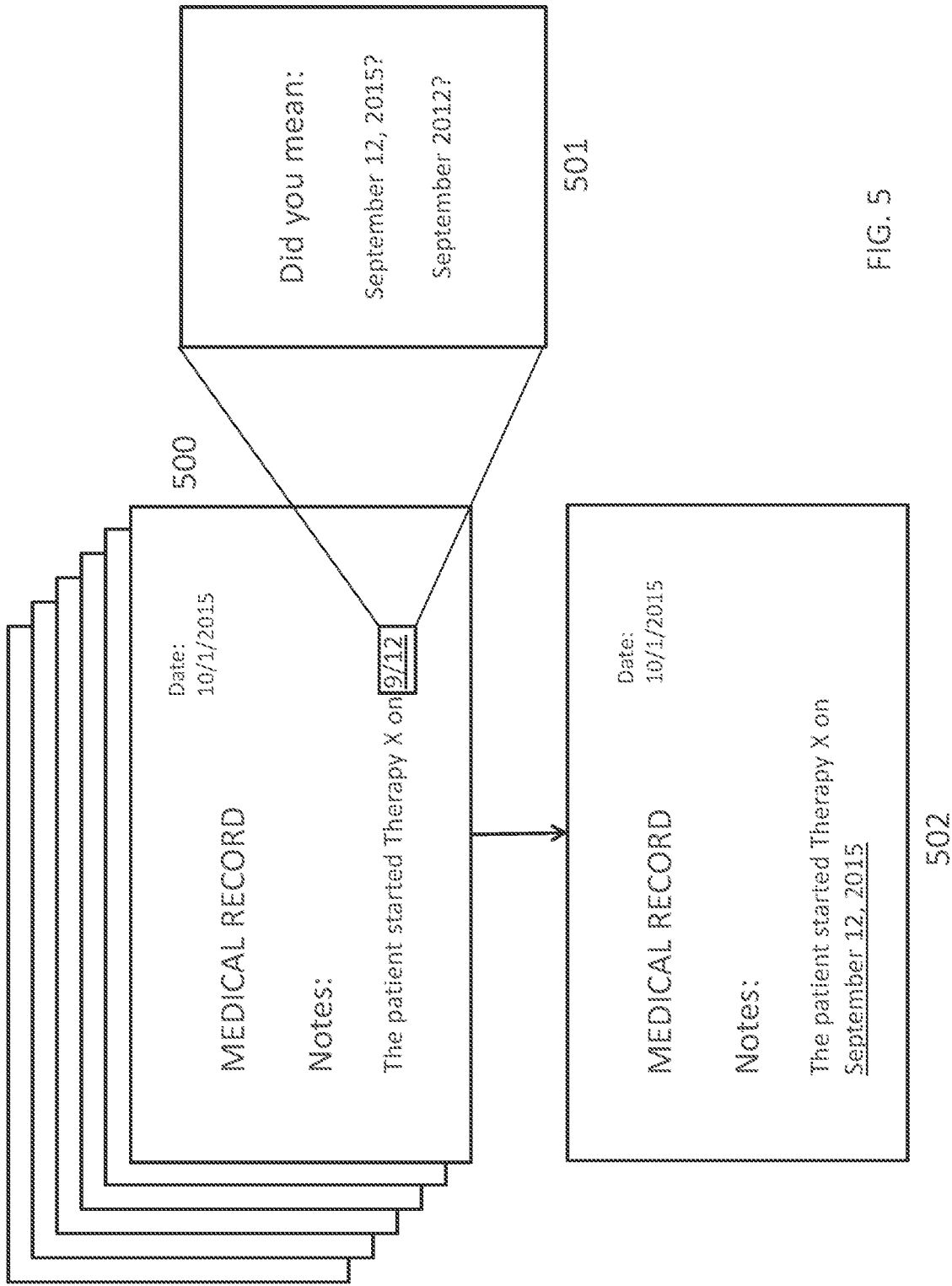
FIG. 5 illustrates an example diagram of an example suggested correction detected by the medical record error detection system based on an ambiguous record entry.

FIG. 5 illustrates an example diagram of an example suggested correction detected by the medical record error detection system based on an ambiguous record entry. Similar to the example as illustrated in FIG. 4, the medical record error detection system can be used to detect and correct entries in medical records that may be ambiguous, i.e. have one or more acceptable interpretations. For instance, a prior medical record 500 may contain a note from a medical professional stating, "The patient started Therapy X on 9/12." "9/12" is ambiguous, as it could be interpreted as September 2012, September $12^{th}$, or, in some date systems, December $9^{th}$. The medical record error detection system can utilize the natural language processing abilities as described above to detect the ambiguous entry and provide a prompt 501 listing the possible interpretations of the ambiguous entry. Through deep analysis of the record elements for each medical record of the patient, the error detection system can rank the possible interpretations based upon their perceived likelihood of correctness. In the present example, the date of the medial record entry is Oct. 1, 2015. Likewise, the error detection system, in processing the previous records of the patient, does not detect the phrase "Therapy X" in any previous medical records. Thus, the error detection system can assign the interpretation of "Sep. 12, 2015" a higher ranking, as it is more likely than not Therapy X was indeed initiated on that date.

The error detection system can refine its rankings of interpretations as the users continue teach the error detection system unambiguous entries. For example, if a particular medical professional is apt to annotate dates by month and year, then the continuing selection of a "September 2012"-type clarification over a "Sep. 12, 2015"-type clarification can cause the error detection system to rank the former clarifications higher on the suggested clarification list when the error detection system detects that the medical record being examined has been created by that particular medical professional.

The system and processes of the figures are not exclusive. Other systems, processes and menus may be derived in accordance with the principles of embodiments described herein to accomplish the same objectives. It is to be understood that the embodiments and variations shown and described herein are for illustration purposes only. Modifications to the current design may be implemented by those skilled in the art, without departing from the scope of the embodiments. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. A computer implemented method, in a data processing system comprising a processor and a memory comprising instructions which are executed by the processor to cause the processor to detect a medical record error, the method comprising:
   training a Question Answering (QA) system to automatically provide an answer to a question;
   receiving, by a cognitive system implementing the QA system, a first question related to one of a corpus of prior medical records from a user;
   transforming, by the cognitive system, the corpus of prior medical records into a plurality of acyclic graphs through natural language processing (NLP), each prior medical record corresponding to a different acyclic graph, wherein nodes of each acyclic graph represent record elements including, medical pathologies and medical actions, and connectors of each acyclic graph represent a sequence of the medical actions;
   receiving, by the cognitive system, a new medical record having a record element inconsistent with an existing record element of the one of the corpus of prior medical records;
   outputting, by the cognitive system, an error message indicating an error of the existing record element due to the inconsistency;
   replacing, by the cognitive system, the existing record element of the one of the corpus of prior medical records with the record element of the new medical record;
   updating, by the cognitive system, an acyclic graph corresponding to the amended existing medical record; and
   providing, by the cognitive system implementing the QA system, the updated acyclic graph to the user as a first answer to the first question.

2. The method as recited in claim 1, wherein the step of transforming further comprises:
   extracting key features of natural language text of the prior medical records;
   transforming the key features into the one or more acyclic graphs;
   wherein the key features include one or more of prescribed pharmaceuticals, performed medical actions, appointment times, ordered diagnostic tests, and terms representing linkages between the key features.

3. The method as recited in claim 1, wherein the corpus of prior medical records and the new medical record correspond to a particular patient.

4. The method as recited in claim 1, wherein the corpus of prior medical records and the new medical record are clinical notes entered by a medical professional.

5. The method as recited in claim 1, further comprising:
   detecting an error in a second record element of the new medical record;
   outputting, based upon an algorithmic analysis by the cognitive system using natural language processing, a list of ranked candidate answers corresponding to suggested corrections of the detected error; and
   modifying the second record element of the new medical record based on the selection of the candidate answer.

6. The method as recited in claim 5, wherein the ranking of the candidate answers is based on one or more previous selections of candidate answers to correct one or more previously detected errors.

7. The method as recited in claim 5, further comprising:
   outputting one or more suggested treatment options based on the modification of the second record element of the new medical record.

8. The method as recited in claim 5, further comprising:
   outputting, along with the list of ranked candidate answers, one or more explanations corresponding to each member of the list of candidate answers having evidentiary information derived from one or more sources of medical information.

9. The method as recited in claim 1, further comprising:
   parsing the first question using NLP to extract keywords and key phrases from the first question;
   classifying the keywords and the key phrases based on a focus of the first question and a lexical answer type (LAT) of the first question;
   formulating one or more queries using the classified keywords and the classified key phrases; and
   applying the one or more queries to the corpus of prior medical records to obtain the one of the corpus of prior medical records having the existing record element.

10. The method as recited in claim 5, wherein the record element of the new medical record and the existing record element correspond to mutually exclusive treatments.

11. The method as recited in claim 10, wherein the record element of the new medical record is acute myeloid leukemia, and the existing record element is acute lymphoblastic leukemia.

12. A computer program product for medical record error detection, the computer program product comprising a computer readable storage medium having program instructions embodied therewith, the program instructions executable by a processor to cause the processor to:
   train a Question Answering (QA) system to automatically provide an answer to a question;
   receive, by a cognitive system implementing the QA system, a first question related to one of a corpus of prior medical records from a user;
   transform, by the cognitive system, the corpus of prior medical records into a plurality of acyclic graphs through natural language processing (NLP), each prior medical record corresponding to a different acyclic graph, wherein nodes of each acyclic graph represent record elements including medical pathologies and medical actions, and connectors of each acyclic graph represent a sequence of the medical actions;
   receive, by the cognitive system, a new medical record having a record element inconsistent with an existing record element of the one of the corpus of prior medical records;
   output, by the cognitive system, an error message indicating an error of the existing record element due to the inconsistency;
   replace, by the cognitive system, the existing record element of the one of the corpus of prior medical records with the record element of the new medical record;
   update, by the cognitive system, an acyclic graph corresponding to the amended existing medical record; and provide, by the cognitive system implementing the QA system, the updated acyclic graph to the user as a first answer to the first question.

13. The computer program product as recited in claim 12, the processor further configured to:
   extract key features of natural language text of the prior medical records;
   transform the key features into the one or more acyclic graphs;
   wherein the key features include one or more of prescribed pharmaceuticals, performed medical actions, appointment times, ordered diagnostic tests, and terms representing linkages between the key features.

14. The computer program product as recited in claim 12, wherein the corpus of prior medical records and the new medical record are clinical notes entered by a medical professional.

15. The computer program product as recited in claim 12, the processor further configured to:
   detect an error in a second record element of the new medical record;
   output, based upon an algorithmic analysis by the cognitive system using natural language processing, a list of ranked candidate answers corresponding to suggested corrections of the detected error; and
   modify the second record element of the new medical record based on the selection of the candidate answer.

16. The computer program product as recited in claim 15, wherein the ranking of the candidate answers is based on one or more previous selections of candidate answers to correct one or more previously detected errors.

17. The computer program product as recited in claim 15, the processor further configured to:
   output one or more suggested treatment options based on the modification of the second record element of the new medical record.

18. The computer program product as recited in claim 15, the processor further configured to:
   output, along with the list of ranked candidate answers, one or more explanations corresponding to each member of the list of candidate answers having evidentiary information derived from one or more sources of medical information.

19. A system for medical record error detection, comprising:
   a processor configured to:
      train a Question Answering (QA) system to automatically provide an answer to a question;
      receive, by a cognitive system implementing the QA system, a first question related to one of a corpus of prior medical records from a user;
      transform, by the cognitive system, the corpus of prior medical records into a plurality of acyclic graphs through a cognitive system by natural language processing (NLP), each prior medical record corresponding to a different acyclic graph, wherein nodes of each acyclic graph represent record elements including medical pathologies and medical actions, and connectors of each acyclic graph represent a sequence of the medical actions;
      receive, by the cognitive system, a new medical record having a record element inconsistent with an existing record element of the one of the corpus of prior medical records;
      output, by the cognitive system, an error message indicating an error of the existing record element due to the inconsistency;
      replace, by the cognitive system, the existing record element of the one of the corpus of prior medical records with the record element of the new medical record;
      update, by the cognitive system, an acyclic graph corresponding to the amended existing medical record; and
      provide, by the cognitive system implementing the QA system, the updated acyclic graph to the user as a first answer to the first question.

* * * * *